United States Patent [19]
Kodo et al.

[11] Patent Number: 6,156,561
[45] Date of Patent: Dec. 5, 2000

[54] SYSTEM AND METHOD FOR CULTURING ALGAE

[75] Inventors: Keiun Kodo; Yasumasa Kodo, both of Mino, Japan

[73] Assignee: Spirulina Biological Lab., Ltd., Osaka, Japan

[21] Appl. No.: 09/118,062

[22] Filed: Jul. 17, 1998

[30] Foreign Application Priority Data

Sep. 16, 1997 [JP] Japan ................................ 9-251043

[51] Int. Cl.⁷ ............................. C12M 1/00; C12M 3/00; C12N 1/12
[52] U.S. Cl. ................... 435/257.1; 435/289.1; 435/292.1; 435/946
[58] Field of Search ................ 435/257.1, 946, 435/289.1, 292.1

[56] References Cited

U.S. PATENT DOCUMENTS

| | | | |
|---|---|---|---|
| 3,768,200 | 10/1973 | Klock | 47/1.4 |
| 5,081,036 | 1/1992 | Familletti | 435/286 |
| 5,176,100 | 1/1993 | Fujino | 119/3 |
| 5,910,254 | 6/1999 | Guelcher et al. | 210/703 |

FOREIGN PATENT DOCUMENTS

WO 97/32818  9/1997  WIPO.

OTHER PUBLICATIONS

Derwent Abstract No. 97–270264/24 and patent document RO 111470 (Cerc TechnologII) Jan. 31, 1996.
Derwent Abstract No. 97–133297/13 and patent document CN 1089991 (Chen Z.) Jul. 27, 1994.
Derwent Abstract No. 95–151469/20 and patent document JP 07–075555 (Hitachi Ltd.) Mar. 20, 1995.
Derwent Abstract No. 94–359745/45 and patent document EP 625570 (NRDC) Nov. 23, 1994.
Derwent Abstract No. 94–068203/09 and patent document JP 06–000079 (Mitsubishi) Jan. 11, 1994.

*Primary Examiner*—David M. Naff
*Assistant Examiner*—Deborah K. Ware
*Attorney, Agent, or Firm*—Arent Fox Kintner Plotkin & Kahn, PLLC

[57] ABSTRACT

A system and method for its use for efficiently culturing algae such as Spirulina are provided. The system comprises a culture pool for exposing a culture fluid containing the algae to sunlight, a culture tank having a larger depth than the culture pool, which is disposed adjacent to the culture pool, a supply unit for supplying the culture fluid from the culture pool to the culture tank, and at least one filter for removing grown algae from the culture fluid overflowing from the culture tank to the culture pool, while allowing to return a filtrate containing immature algae to the culture pool. It is preferred that this system further comprises a unit for mixing a gas containing carbon dioxide in the culture fluid to be supplied in the culture tank, and a lighting unit disposed in the culture tank to provide an artificial light to the culture fluid. In this case, it is possible to carry out the photosynthesis of the algae night and day.

15 Claims, 7 Drawing Sheets

SYSTEM AND METHOD FOR CULTURING ALGAE

BACKGROUND OF THE INVENTION

1. Field of the Invention

The present invention relates to a system for efficiently culturing algae such as Spirulina and a method of culturing the algae by using the system.

2. Disclosure of the Prior Art

Spirulina is a kind of blue-green algae living at salt lakes in the tropical regions. For example, it is well known that Spirulina lives in the Chad Lake of the Republic of Chad located at the Sahara Desert of Africa. Tribes living around the Chad Lake have ingested Spirulina as a protein source from time immemorial. The protein of Spirulina is composed of a lot of amino acids essential to human being, and richly contains minerals and nutrient substances except for vitamin C. Thus, Spirulina is drawing public attention as a nutrition-supplementary food for keeping human health. In addition, plans for using Spirulina as the protein source in space is in progress in National Aerospace Laboratory in Japan and NASA.

By the way, general crops are harvested once or twice a year. However, Spirulina can be harvested every time period of 5 to 20 days. When suitable conditions are selected, it is possible to harvest Spirulina 50 times or more a year. Therefore, Spirulina is expected as one means for solving the food problem of the earth. Additionally, since Spirilina has 6 to 8 times oxygen generating capability than general plants during photosynthesis, it has been used in CLESS (Controlled Life and Ecological Support System) on a space station project of NASA.

Spirulina has been usually cultured in various world places under a natural growth condition by the use of a culture pool, which has a relatively shallow depth for exposing a culture fluid containing algae to sunlight. For example, an upper-opened type pool having a width of about 10 m, a length of about 50 m and a depth of 20 to 25 cm is used as the culture pool. In addition, the pool has a separation board extending in the lengthwise direction at a substantially center of the width thereof to make a circulation way of the culture fluid in the pool. Spirulina can be cultured in the pool according to the following method. First, the pool is filled with the culture fluid containing Spirulina. Then, a circulation of the culture fluid along the circulation way in the pool is performed by stirrers, while sunlight being radiated to the culture fluid. In this time, carbon dioxide gas required for the photosynthesis of Spirulina is continuously supplied to the culture fluid by a pump. After the elapse of 5 to 20 days, Spirulina grows up to 300 $\mu$m or more. The grown Spirulina is removed together with immature Spirulina from the culture fluid by a filtration.

By the way, only sunlight is used in this culturing method. Therefore, the growth rate of Spirulina lowers during the nighttime, or when it is cloudy day or rainy day. In addition, since the grown Spirulina floating in the culture fluid deteriorates the transmittance of sunlight into the culture fluid, a sufficient amount of sunlight required for the photosynthesis does not reach the immature Spirulina in the bottom of the culture pool. When a heavy rain or flood disaster happens, there is a possibility that most of the grown Spirulina is lost by an overflow of the culture fluid from the culture pool. Moreover, since the culture pool is usually designed to have a relatively small depth, there is a problem that carbon dioxide gas supplied from the bottom of the culture pool passes through the culture fluid without being sufficiently absorbed by the culture fluid. Since the above culturing method is based on a batch operation, the culturing of the immature Spirulina must be stopped every harvest time of the grown Spirulina.

SUMMARY OF THE INVENTION

The present invention is to provide a system for efficiently culturing algae such as Spirulina. That is, the system comprises a culture pool for exposing a culture fluid containing the algae to sunlight, a culture tank having a larger depth than the culture pool, which is disposed adjacent to the culture pool, a supply unit for supplying the culture fluid from the culture pool to the culture tank, and at least one filter for removing grown algae from the culture fluid overflowing from the culture tank to the culture pool, while allowing to return a filtrate containing immature algae to the culture pool.

The culture pool is usually designed to have a relatively small depth for exposing the culture fluid containing the algae to sunlight. Therefore, a big tract of land is needed to construct the culture pool. Since the present system uses a circulation of the culture fluid between the culture pool and the culture tank having the larger depth than the culture pool, it is possible to construct the culture pool in a relatively small tract of land. This provides an economical use of the land without lowering the culturing efficiency of the system. In addition, as indicated above, when a heavy rain happens, there is a possibility of losing most of the culture fluid in the culture pool by overflow. In the present system, since a part of the culture fluid is stored by the culture tank, it is possible to readily restart the culturing of the algae after the heavy rain. Moreover, since the grown algae can be continuously harvested from the culture fluid by the filter, and the filtrate containing the immature algae are returned to the culture pool, it is possible to keep a good transmittance of sunlight into the culture fluid of the culture pool.

In a preferred embodiment of the present invention, the system further comprises a mixing unit attached to the supply unit to mix a gas containing carbon dioxide in the culture fluid, and a lighting unit disposed in the culture tank to provide an artificial light to the culture fluid. This system can provide an optimum condition for the photosynthesis of the algae in the culture tank during the nighttime, so that the algae can be efficiently cultured night and day. In addition, the mixing and lighting units would be useful to maintain the culturing efficiency of the algae when the supply amount of sunlight decreases.

In a further preferred embodiment of the present invention, the supply unit comprises a supply pipe extending from the culture pool to a bottom of the culture tank, and a pump attached to the supply line. Since the culture fluid containing carbon dioxide gas is supplied from the bottom of the culture tank, it is possible to dissolve a sufficient amount of carbon dioxide into the culture fluid. This enhances the photosynthesis of the algae.

It is preferred that a volume of the culture tank is at least 0.5 times larger than that of the culture pool.

It is preferred that filter a plurality of filters having different meshes are used to harvest remove the grown algae.

It is further preferred that the culture tank comprises an optical fiber bundle for introducing sunlight into the culture tank and a traveling unit for traveling the bundle along a predetermined route in the culture tank.

It is also preferred that the culture pool has a depth of 0.2 m to 0.25 m, and the culture tank has a depth of 1 m to 3 m.

It is another object of the present invention to provide a method of culturing algae such as Spirulina. The method comprises the steps of supplying a culture fluid containing the algae from a culture pool for exposing the culture fluid to sunlight to a culture tank having a larger depth than the pool which is disposed adjacent to the culture pool, removing grown algae from the culture fluid overflowing from the culture tank to the culture pool by filtration, and returning a filtrate containing immature algae to the culture pool.

These and still other objects and advantages will become apparent from the following detail descriptions of the preferred embodiments and examples of the invention when taken in conjunction with the attached drawings.

DETAIL DESCRIPTION OF THE PREFERRED EMBODIMENTS

Figure 1:
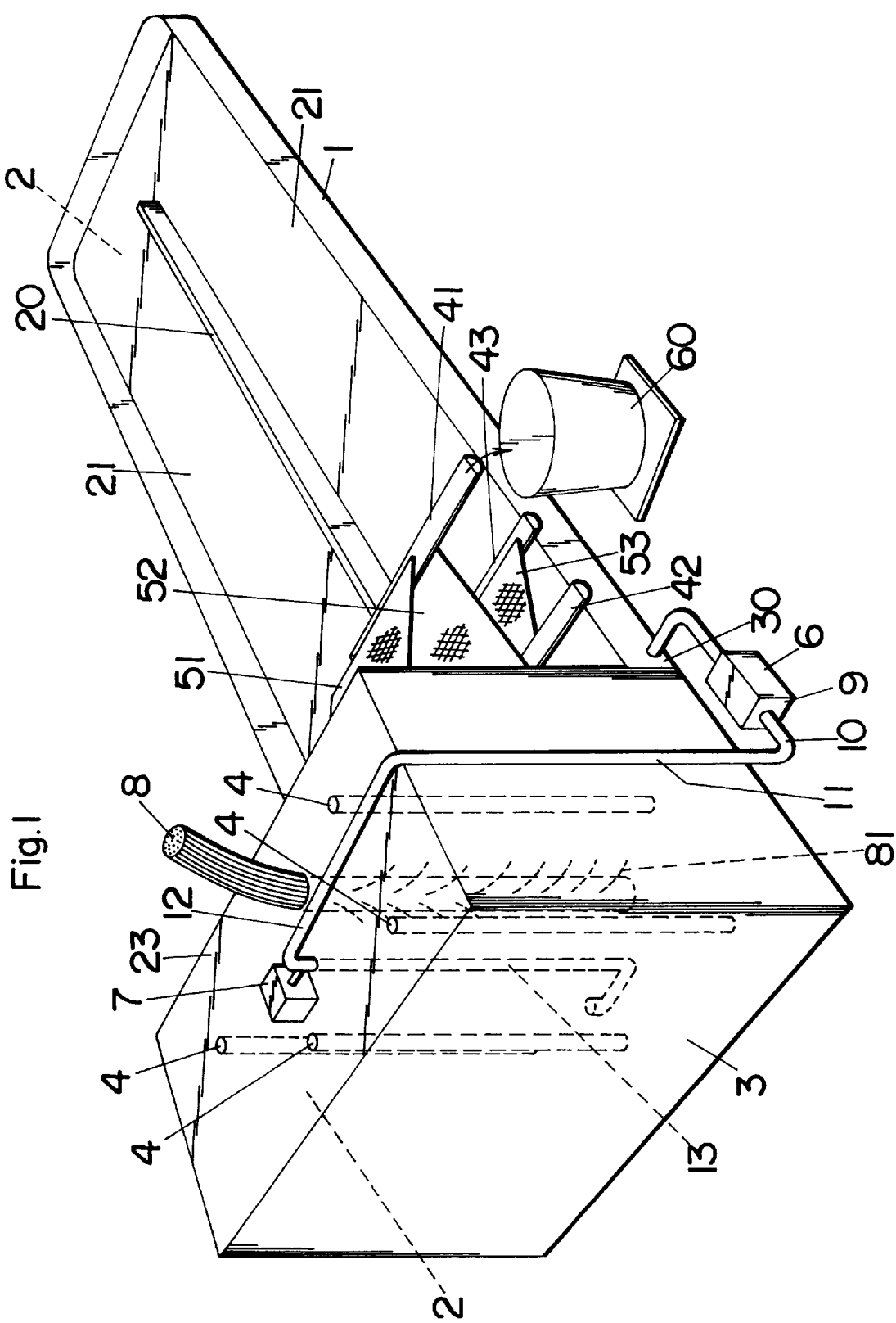
FIG. 1 is a perspective view of a system for culturing algae such as Spirulina of the present invention.

As a preferred embodiment of the present invention, a system for efficiently culturing Spirulina is explained in detail.

In this embodiment, an upper-opened type pool having a width of about 10 m, a length of about 50 m and a depth of 0.2 to 0.25 m is used as a culture pool 1 for exposing a culture fluid 2 containing Spirulina to sunlight. Thus, the culture pool should be formed to have the large length and width and the small depth so that sunlight is efficiently and uniformly supplied to the culture fluid 2. In addition, the pool 1 has a separation board 20 extending in the lengthwise direction at a substantially center of the width thereof to make a circulation way 21 in the pool. Wing-type stirrers 22 are disposed to make a circulation of the culture fluid 2 along the circulation way 21 in the culture pool 1, as shown by arrows in FIG. 2A. For example, the stirrers 22 may be intermittently operated for a short time period of 1 to 5 minutes to transfer Spirulina on the bottom of the culture pool to the surface of the culture fluid.

A culture tank 3 formed in a box shape having a top opening 23 is disposed adjacent to the culture pool 1. In this embodiment, the culture tank 3 is made of concrete and has a width of about 10 m, a length of about 6 m and a depth of 2 m. Thus, it is preferred to form the culture tank 3 to have the relative small length and width and the depth much larger than the culture pool. It is also preferred that the culture tank 3 is formed such that a volume of the culture tank is 0.5 to 4 times larger than that of the culture pool 1. The culture tank 3 is filled with the culture fluid 2. If necessary, a detachable roof member (not shown) made of a transparent material can be attached to the top opening of the culture tank 3. The culture tank 3 may be made of a transparent material to allow the culture tank to easily take in sunlight. It is also preferred to provide a control unit for controlling a temperature of the culture fluid in the culture tank 3. For example, the control unit may comprise an electric heater (not shown) for warming the culture fluid at a temperature of 25 to 35° C. in winter season. The control unit is useful to maintain an optimum temperature condition for culturing Spirulina all the year.

Figure 3:
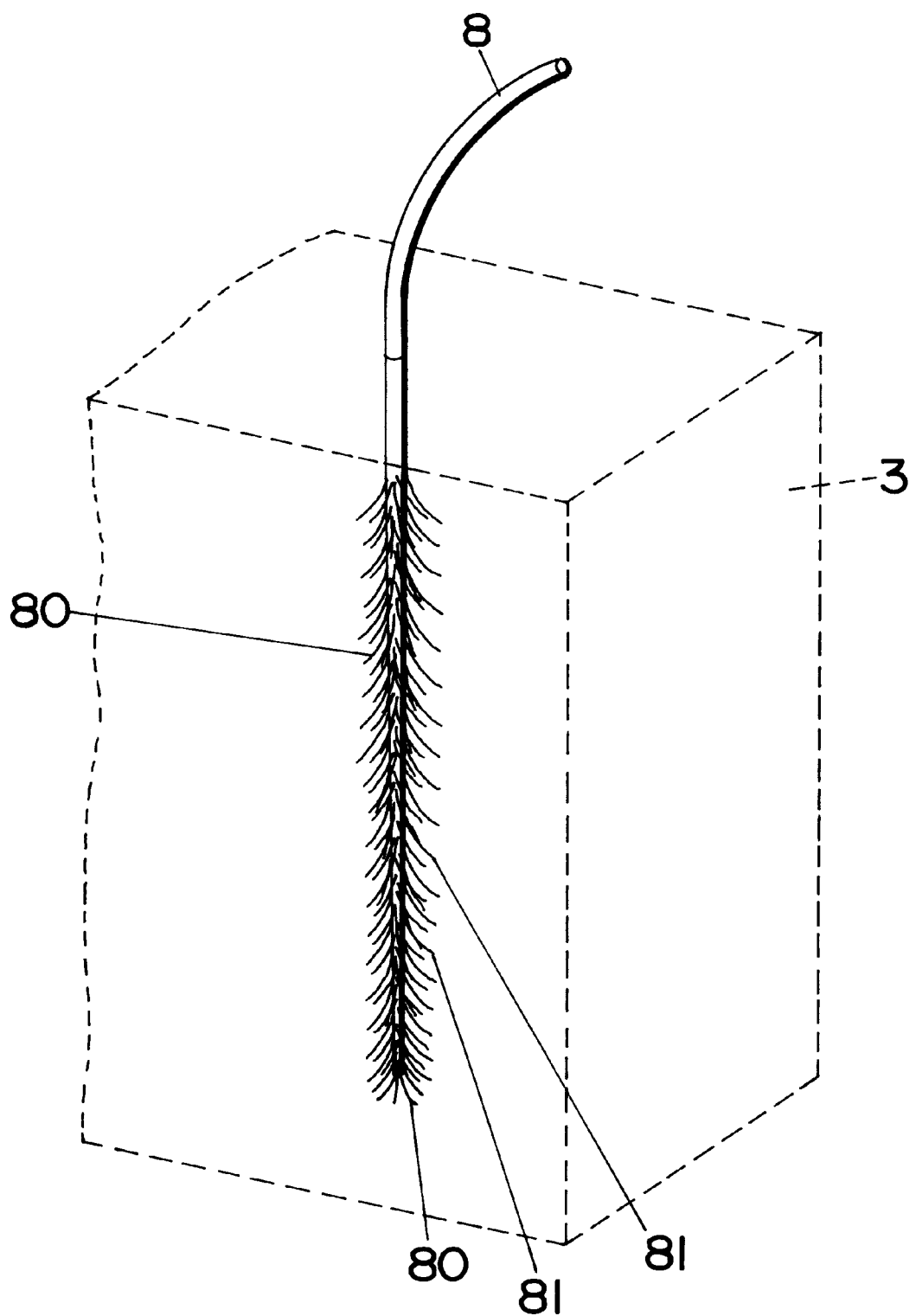
FIG. 3 is a schematic of an optical fiber bundle of the system of FIG. 1.

A lighting unit 4 is disposed in the culture tank 3 to supply an artificial light required for the photosynthesis of Spirulina during the nighttime. For example, a plurality of fluorescent lamps, sodium-vapor lamps, or light-emitting diodes can be used as the lighting unit 4. In this case, the fluorescent lamps 4 are disposed in the culture tank 3 to extend in the perpendicular direction so as to be spaced away from each other by a predetermined distance. In this case, it is preferred that the fluorescent lamps 4 have a length of about two third of the depth of the culture tank 3. In addition, the culture tank 3 comprises at least one optical fiber bundle 8 for supplying sunlight to the culture fluid therein. The optical fiber bundle 8 is formed with 50 to 100 optical fibers 80. The optical fibers 80 have different lengths so that sunlight-radiation ends 81 of the optical fibers are uniformly distributed with respect to the depth direction of the culture tank 3, as shown in FIG. 3. The optical fiber bundle 8 can be moved along a predetermined route in the culture tank 3 by a traveling unit (not shown) to achieve a uniform radiation of sunlight to the culture fluid 2 in the culture tank 3.

The culture fluid is sent from the culture pool 1 to the culture tank 3 by a supply unit 9. The supply unit comprises a supply pipe 10 extending therebetween and a screw pump 6. One end of the supply pipe 10 is connected to a fluid stagnant portion 30 of the culture pool 1. The other end of the supply pipe 10 is disposed at the vicinity of a bottom of the culture tank 3. As shown in FIG. 1, this supply pipe 10 is designed to prevent a back current of the culture fluid when the operation of the screw pump 6 is stopped. That is, the supply pipe 10 comprises a first section 11 extending in a perpendicular direction along a side wall of the culture tank 3, a second section 12 extending in a horizontal direction towards a substantially center of the top opening 23 of the culture tank 3, and a third section 13 extending in the culture tank 3 in the perpendicular direction. An aspirator 7 for mixing the air including carbon dioxide in the culture fluid to be supplied into the culture tank 3 is connected to the supply pipe 10 at substantially a corner between the second and third sections 12, 13. As a result, it is possible to provide a sufficient amount of carbon dioxide required for the photosynthesis of Spirulina to the culture fluid in the culture tank 3.

Figure 4:
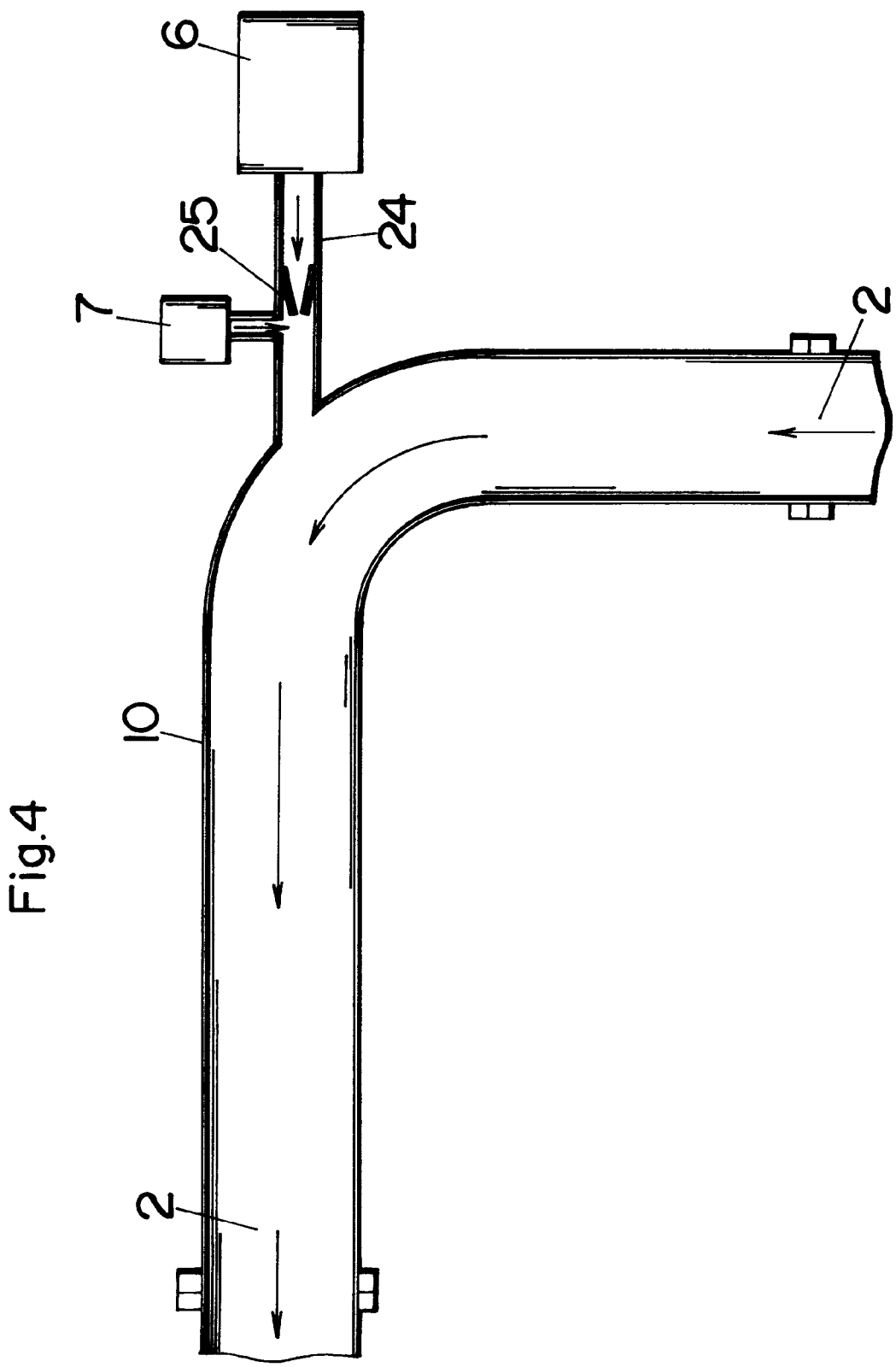
FIG. 4 is a schematic of a jet pump.

As shown in FIG. 4, a jet pump can be used in place of the screw pump 6. A pressurized water is supplied to the culture fluid 2 passing the supply pipe from a water induction pipe 24, so that the culture fluid is sent into the culture tank 3 by the pressurized water. The aspirator 7 is attached to the water induction pipe 24 to mix the air in the pressurized water. Numeral 25 designates a non-return valve for preventing a back current of the pressurized water. In addition, it is possible to use a conventional piston pump, screw conveyer, and so on.

Figure 2:
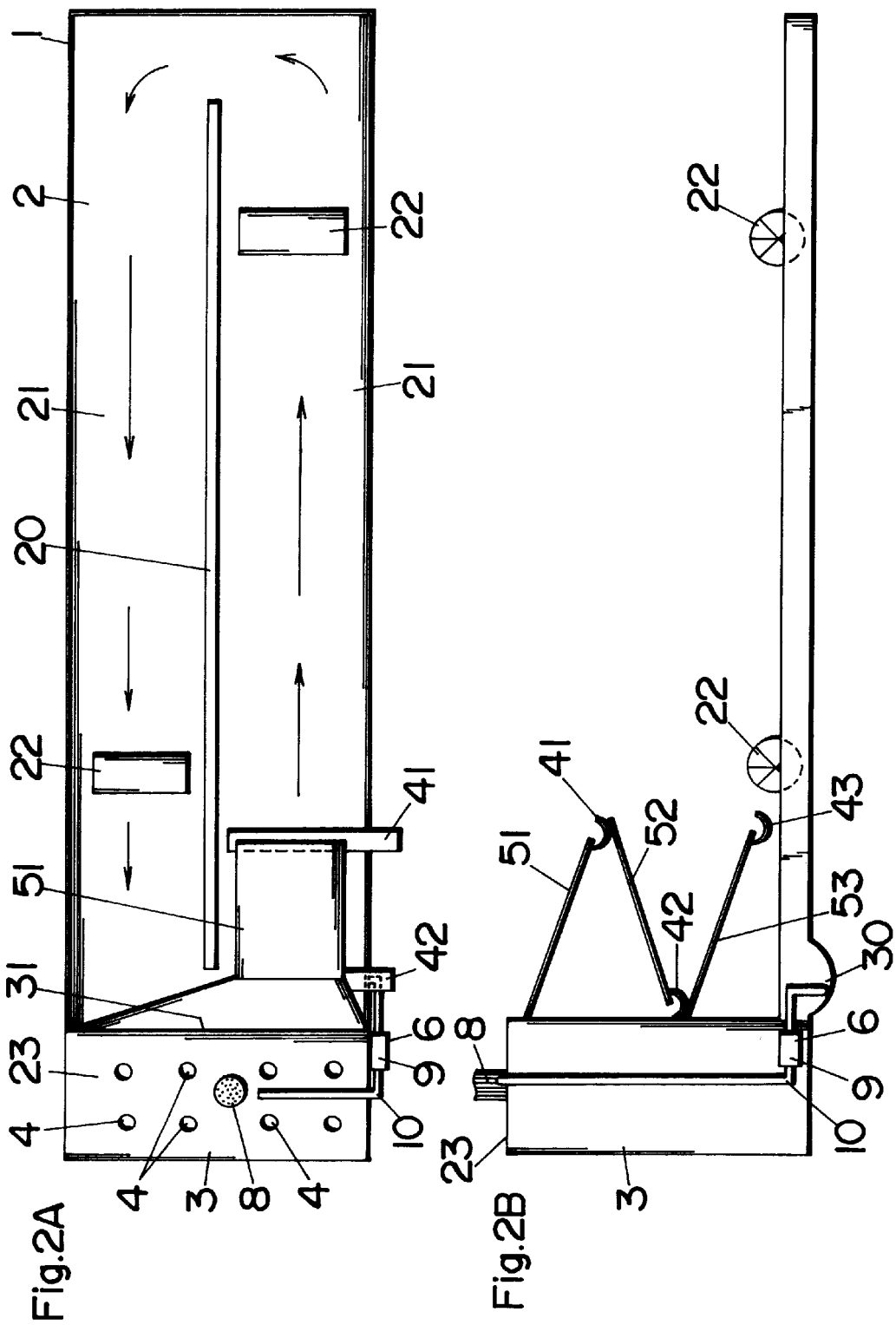
FIGS. 2A and 2B are top and side views of the system of FIG. 1, respectively.

In this system, three filters (51, 52, 53) having different meshes are used to harvest a grown Spirulina from the culture fluid 2. The filters are disposed above the culture pool 1 and adjacent to the culture tank 3 to remove the grown Spirulina from the culture fluid 2 overflowing from the culture tank to the culture pool through the top opening 23. That is, as shown in FIG. 2B, a first filter 51 having a large mesh for catching the grown Spirulina having a size of 300 $\mu$m or more is disposed to obliquely extend from a top edge portion 31 of the culture tank 3 to a first conduit 41 placed above the culture pool 1. An overflow of the culture fluid 2 from the culture tank 3 is supplied to the first filter 51 through the edge portion 31. The Spirulina caught by the first filter 51 is collected to a vessel 60 through the first conduit 41.

A second filter 52 having a medium mesh for catching the grown Spirulina having a size of 200 to 300 μm is disposed just under the first filter 51. As shown in FIG. 2B, the second filter 52 obliquely extends from a position just under the first conduit 41 to a second conduit 42 placed adjacent to the culture tank 3. The Spirulina caught by the second filter 52 is collected to a vessel (not shown) through the second conduit 42.

A third filter 53 having a small mesh for catching the grown Spirulina having a size of 100 to 200 μm is disposed just under the second filter 52. As shown in FIG. 2B, the third filter 53 obliquely extends from a position just under the second conduit 42 to a third conduit 43 placed between the first conduit 41 and the culture pool 1. The Spirulina caught by the third filter 53 is collected to a vessel (not shown) through the third conduit 43. Thus, there is an advantage that the grown Spirulina can be readily grouped into three classes with respect to the growth size of Spirulina. In addition, it is possible to continuously harvest the grown Spirulina without stopping the culturing of Spirulina.

A filtrate passing through the third filter 53, in which an immature Spirulina having a size of 100 μm or less is contained, is returned to the culture pool 1. Therefore, the culturing of the immature Spirulina is started again in the culture pool 1. Since a light transmittance of the returned culture fluid 2 is favorably maintained by the removal of the grown Spirulina by the filters (51, 52, 53), it is possible to efficiently supply sunlight to the immature Spirulina in the culture fluid flowing on the bottom of the culture pool 1 along the circulation way 21. In this embodiment, the three different filters are used to harvest the grown Spirulina, however, the number of the filters and mesh sizes of the filters are not limited to the above explanation.

Next, a method of efficiently culturing Spirulina by using the above system of the present invention is explained in detail. As the culture fluid 2 containing Spirulina, for example, a mixture of Spirulina and one of compositions S1 to S3 listed in Table 1 can be used. The culture pool 1 and the culture tank 3 are filled with the culture fluid 2. The culture fluid in the culture pool 1 is exposed to sunlight. A part of the culture fluid 2 is transferred from the culture pool 1 to the culture tank 3 by the supply unit 9. For example, a supply rate of the culture fluid into the culture tank may be 1 to 10 ton/min.

TABLE 1

| Composition | S1 | S2 | S3 |
| --- | --- | --- | --- |
| $KNO_3$ | 3.0 | — | — |
| $NaNO_3$ | — | 2.5 | 1.5 |
| $K_2HPO_4$ | 1.0 | 0.5 | 0.5 |
| $K_2SO_4$ | 1.0 | 1.0 | 1.0 |
| $NaHCO_3$ | 16.0 | 16.8 | 4.5 |
| NaCl | 1.5 | 1.0 | 1.0 |
| $MgSO_4.7H_2O$ | 0.02 | 0.2 | 0.2 |
| $CaCl_2.2H_2O$ | 0.04 | 0.04 | 0.04 |
| EDTA.2Na | 0.064 | 0.08 | — |
| $FeSO_4.7H_2O$ | 0.008 | 0.01 | 0.01 |
| $Na_2SO_4.10H_2O$ | 3.5 | — | — |
| Ferric Citrate | O.012 | — | — |
| Water | 1000.0 | 1000.0 | 1000.0 |

(Unit: parts by weight)

In this time, the air is mixed in the culture fluid 2 to be supplied into the culture tank 3 by the aspirator 7. The culture fluid containing the air is supplied into the culture tank 3 at the bottom of the culture tank. Since the air contained in the culture fluid gradually migrates in the culture fluid 2 from the bottom towards the top opening of the culture tank 3, it is possible to dissolve a sufficient amount of carbon dioxide of the air into the culture fluid 2 of the culture tank 3. In this time, if necessary, sunlight is radiated to the culture fluid 2 through the optical fiber bundle 8. In the nighttime, an artificial light can be provided to the culture fluid 2 by the lighting unit 4. Thus, the present system allows performing the photosynthesis of Spirulina in the culture tank 3 night and day.

The grown Spirulina is collected from an overflow of the culture fluid 2 of the culture tank 3 by the first, second and third filters (51, 52, 53). The filtrate passing through the first filter 51, the second filter 52 and the third filter 53, contains the immature Spirulina. The filtrate is returned to the culture pool 1. The returned filtrate is mixed with the culture fluid flowing along the circulation way 21 of the culture pool 1.

Figure 5:
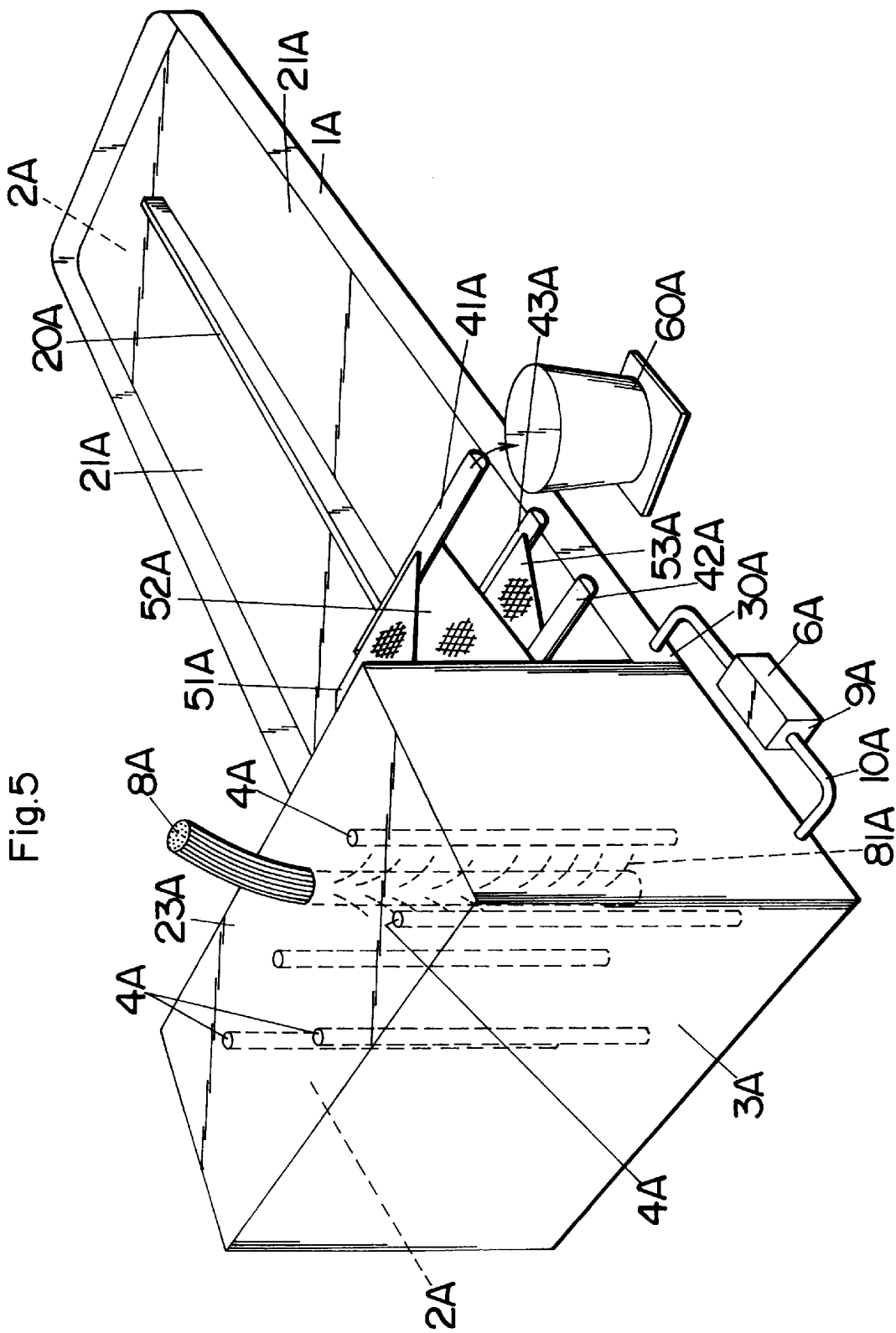
FIG. 5 is a perspective view of a modification of the system of FIG. 1.
Figure 6:
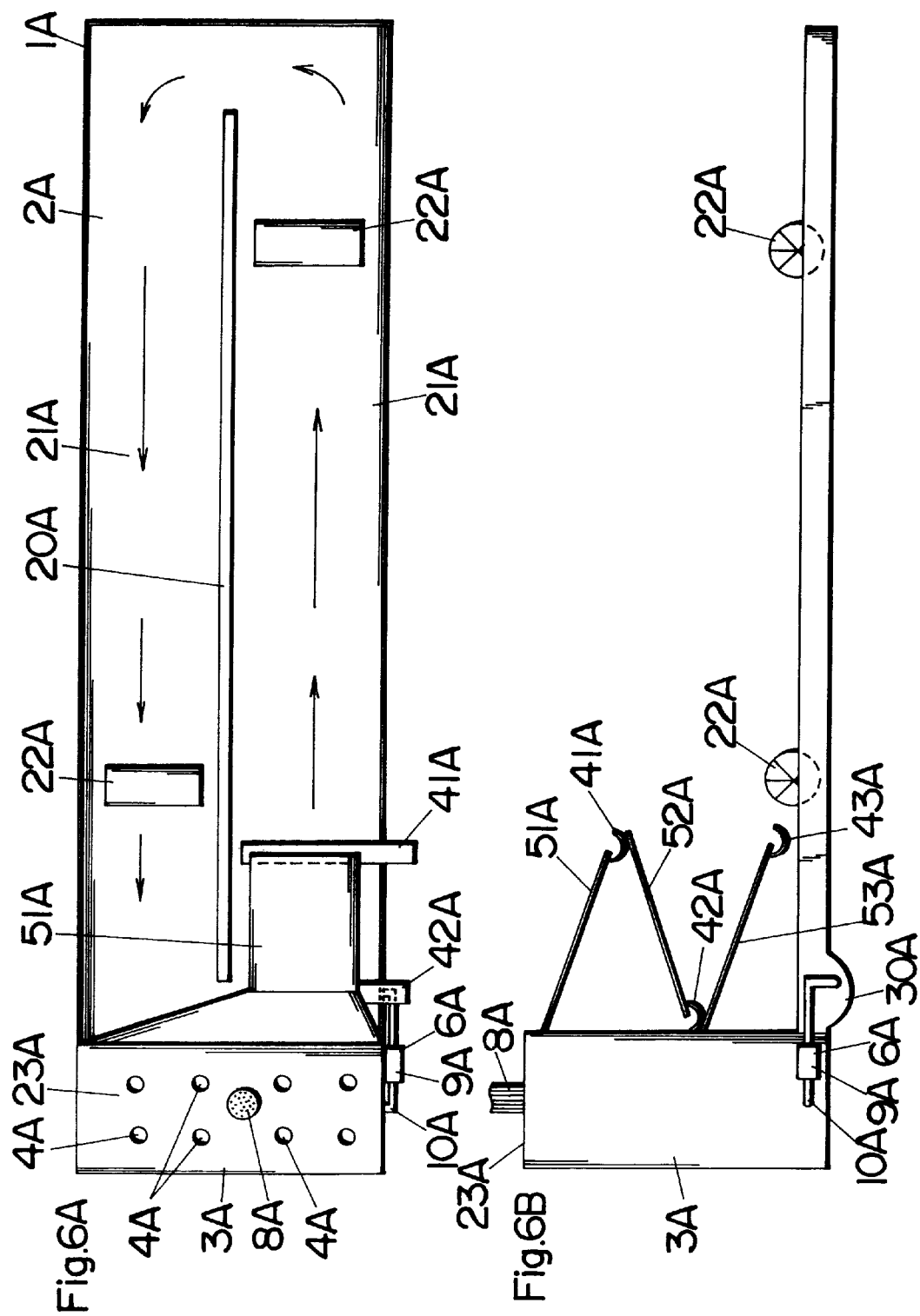
FIGS. 6A and 6B are top and side views of the system of FIG. 5, respectively.

As a modification of the above embodiment, a culture pool 1A may be connected to a lower portion of a side wall of a culture tank 3A by a supply pipe 10A, as shown in FIGS. 5, 6A and 6B. In addition, a pneumatic pump 6A is used to directly supply the culture fluid including the air to the bottom of the culture tank 3A and induce an ascending current of the culture fluid in the culture tank. Therefore, no duplicate explanation to common parts is deemed necessary. Like parts are designated by numerals with a suffixed letter of "A".

Figure 7:
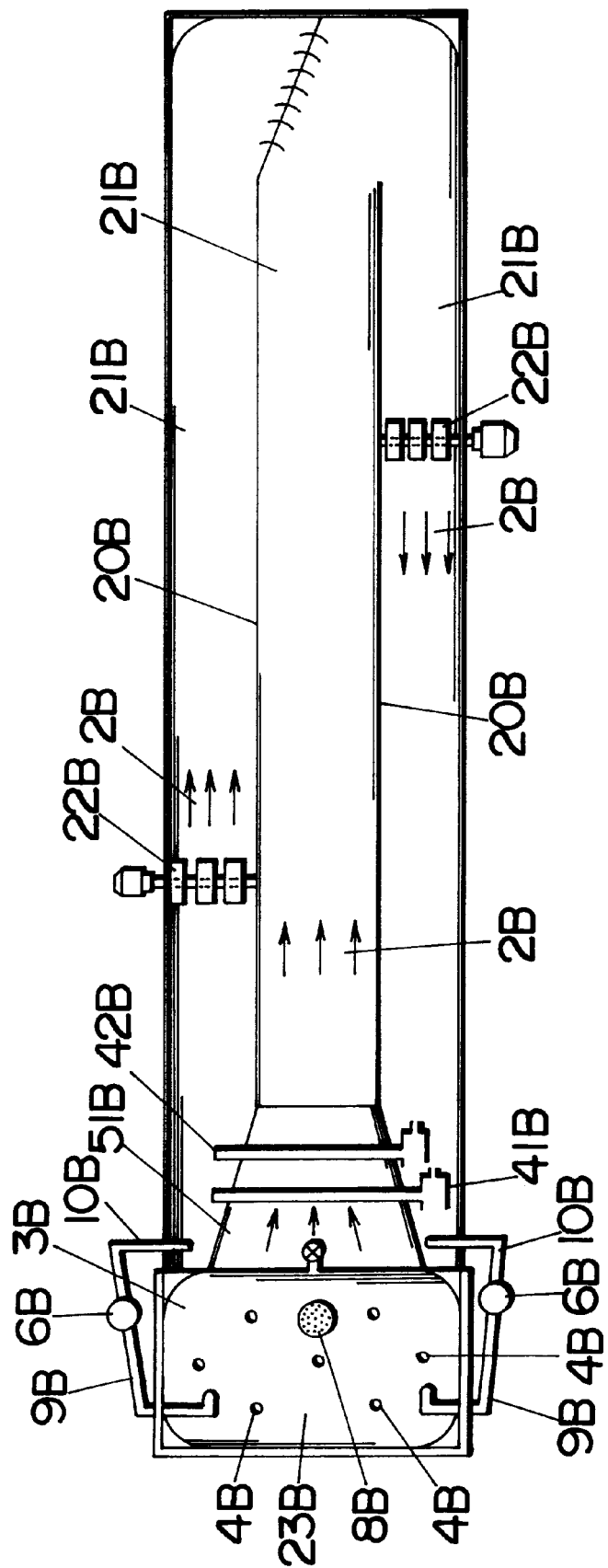
FIG. 7 is a top view of a system for culturing algae such as Spirulina of the present invention.

As another embodiment of the present invention, a system for culturing algae such as Spirulina is shown in FIG. 7. This system is substantially the same as that of FIG. 1 except that a circulation way 21B formed in a culture pool 1B is composed of three rows, and that a culture fluid 2B is supplied from the culture pool into a culture tank 3B by a pair of supply pipes 10B. Therefore, no duplicate explanation to common parts is deemed necessary. Like parts are designated by numerals with a suffixed letter of "B".

EXAMPLE 1

A culturing system of the type shown in FIG. 1 was used to culture Spirulina. A culture pool of the system has a width of 10 m, a length of 50 m and a depth of 0.25 m. A culture tank of the system is made of a transparent material and has a width of 10 m, a length of 6 m and a height of 2 m. Each of the culture pool and the culture tank was filled with 100 tons of a culture fluid not containing Spirulina. 3 $m^3$ of an additional culture fluid containing Spirulina previously prepared in a laboratory was mixed to the culture fluid in each of the culture pool and the culture tank. Then, the culture fluid was circulated between the culture pool and the culture tank for 10 days. A supply rate of the culture fluid from the culture pool to the culture tank is 5 ton/min. In the culture pool, a circulation of the culture fluid along a circulation way was continued for the 10 days. Only sunlight was radiated to the culture fluid for the 10 days without using an artificial light. After the elapse of the 10 days, a harvest amount of a grown Spirulina having a size of 300 μm or more was measured. Results are listed in Table 2.

EXAMPLE 2

A culturing system used in Example 2 is substantially the same as that of Example 1 except that the culture tank is made of concrete. A culturing method performed in Example 2 is substantially the same as that of Example 1 except that an artificial light of fluorescent lamps was radiated to the culture fluid in the culture tank night and day for 10 days. After the elapse of the 10 days, a harvest amount of a grown Spirulina having a size of 300 μm or more was measured. Results are listed in Table 2.

EXAMPLE 3

A culturing system used in Example 3 is the same as that of Example 1. A culturing method performed in Example 3 is substantially the same as that of Example 1 except that an artificial light of fluorescent lamps was radiated to the culture fluid in the culture tank only for the nighttime, i.e., 12 hours from 6 P.M. to 6 A.M. every day for 10 days, and only sunlight was radiated to the culture fluid for the daytime, i.e., 12 hours from 6 A.M. to 6 P.M. every day for the 10 days. After the elapse of the 10 days, a harvest amount of a grown Spirulina having a size of 300 μm or more was measured. Results are listed in Table 2.

EXAMPLE 4

A culturing system used in Example 4 is the same as that of Example 2. A culturing method performed in Example 4 is the same as that of Example 3. After the elapse of 10 days, a harvest amount of a grown Spirulina having a size of 300 μm or more was measured. Results are listed in Table 2.

COMPARATIVE EXAMPLE 1

A culturing system used to culture Spirulina in Comparative Example 1 does not have a culture tank. The system only has an upper-opened type pool having a width of 10 m, a length of 50 m and a depth of 0.25 m. The culture pool was filled with 100 tons of a culture fluid not containing Spirulina. 3 m³ of an additional culture fluid containing Spirulina previously prepared in a laboratory was mixed to the culture fluid in the culture pool. In the culture pool, a circulation of the culture fluid along a circulation way was continued for 10 days. Only sunlight was radiated to the culture fluid for the 10 days. After the elapse of the 10 days, a harvest amount of a grown Spirulina having a size of 300 μm or more was measured. Results are listed in Table 2.

The results listed in Table 2 show that the harvest amount of the grown Spirulina of 300 μm or more in each of Examples 1 to 4 is much larger than that of Comparative Example 1. The fact proves that the algae such as Spirulina can be efficiently cultured by using the system of the present invention.

TABLE 2

|  | Radiation of Artificial Light | | Harvest Amount of Spirulina of 300 μm or more |
|---|---|---|---|
|  | Daytime (6 A.M.–6 P.M.) | Nighttime (6 P.M.–6 A.M.) |  |
| Example 1 | X | X | 74 |
| Example 2 | ◯ | ◯ | 152 |
| Example 3 | X | ◯ | 125 |
| Example 4 | X | ◯ | 143 |
| Comparative Example 1 | X | ◯ | 40 |

LIST OF REFERENCE NUMERALS

| 1 | culture pool |
|---|---|
| 2 | culture fluid |

-continued

LIST OF REFERENCE NUMERALS

| 3 | culture tank |
|---|---|
| 4 | lighting unit |
| 6 | screw pump |
| 7 | aspirator |
| 8 | optical fiber bundle |
| 9 | supply unit |
| 10 | supply pipe |
| 11 | first section |
| 12 | second section |
| 13 | third section |
| 20 | separation board |
| 21 | circulation way |
| 22 | stirrer |
| 23 | top opening |
| 24 | water induction pipe |
| 25 | non-return valve |
| 30 | fluid stagnant portion |
| 31 | top edge portion |
| 41 | first conduit |
| 42 | second conduit |
| 43 | third conduit |
| 51 | first filter |
| 52 | second filter |
| 53 | third filter |
| 60 | vessel |
| 80 | optical fiber |
| 81 | sunlight-radiation end |
| 1A | culture pool |
| 3A | culture tank |
| 6A | pneumatic pump |
| 10A | supply pipe |
| 1B | culture pool |
| 2B | culture fluid |
| 3B | culture tank |
| 10B | supply pipe |
| 21B | circulation way |

What is claimed is:

1. A system for culturing algae comprising:
a culture pool for exposing a culture fluid containing said algae to sunlight;
a culture tank having a larger depth than said pool, which is disposed adjacent to said pool;
a supply means for supplying said culture fluid from said pool to said tank; and
at least one filter means disposed outside of said culture tank and above said culture pool such that said at least one filter means receives said culture fluid overflowed from said culture tank for removing grown algae from said culture fluid and a filtrate containing immature algae passing through said at least one filter means is returned to said pool.

2. The system as set forth in claim 1 further comprising a means for mixing a gas containing carbon dioxide in said culture fluid to be supplied in said tank, and a lighting means disposed in said tank to provide an artificial light to said culture fluid.

3. The system as set forth in claim 1, wherein said supply means comprises a supply pipe extending from said pool to a bottom of said tank, and a pump attached to said supply pipe.

4. The system as set forth in claim 1, wherein said tank comprises a lighting means for radiating an artificial light to said culture fluid.

5. The system as set forth in claim 1, wherein a volume of said tank is at least 0.5 times larger than that of said pool.

6. The system as set forth in claim 1, wherein said filter means is composed of a plurality of filters having different meshes.

7. The system as set forth in claim 1, wherein said tank comprises an optical fiber bundle for introducing sunlight into said tank and a means for traveling said bundle along a predetermined route in said tank.

8. The system as set forth in claim 1, wherein said culture pool has a depth of 0.2 m to 0.25 m, and said culture tank has a depth of 1 m to 3 m.

9. A method of culturing algae using the system set forth in claim 1, said method comprising the steps of:

supplying a culture fluid containing said algae from said culture pool to said culture tank;

removing grown algae from said culture fluid overflowed from said tank by said filter means; and returning a filtrate containing immature algae to said culture pool.

10. The method as set forth in claim 9, further comprising the step of radiating an artificial light to said algae in said tank.

11. The method as set forth in claim 9, wherein a volume of said tank is at least 0.5 times larger than that of said pool.

12. The method as set forth in claim 9, wherein said removing step is performed by using a plurality of filters having different meshes.

13. The method as set forth in claim 9, further comprising the step of radiating sunlight provided through an optical fiber bundle to said algae in said tank while traveling said bundle along a predetermined route in said tank.

14. A system for culturing algae comprising:

a culture pool for exposing a culture fluid containing said algae to sunlight;

a culture tank having a larger depth than said pool, which is disposed adjacent to said pool;

a supply means for supplying said culture fluid from said pool to said tank;

at least one filter means disposed at the outside of said culture tank and above said culture pool such that said at least one filter means receives said culture fluid overflowed from said culture tank to remove grown algae from said culture fluid and the filtrate containing immature algae passing through said at least one filter means is returned to said culture pool; and an optical fiber bundle disposed in said culture tank to radiate a light to said culture fluid in said culture tank, said bundle comprising optical fibers having different lengths such that light-radiation ends of said optical fibers are uniformly distributed with respect to a depth direction of said culture tank.

15. The system as set forth in claim 14, wherein said optical fiber bundle radiates sunlight to said culture fluid in said culture tank.

* * * * *